US008383721B2

(12) United States Patent
Lewandowski et al.

(10) Patent No.: US 8,383,721 B2
(45) Date of Patent: Feb. 26, 2013

(54) POLYMERIZABLE IONIC LIQUID COMPOSITIONS

(75) Inventors: Kevin M. Lewandowski, Inver Grove Heights, MN (US); Jason D. Clapper, Lino Lakes, MN (US); Joel D. Oxman, Minneapolis, MN (US); Larry R. Krepski, White Bear Lake, MN (US); Peiwang Zhu, Woodbury, MN (US); Yizhong Wang, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 102 days.

(21) Appl. No.: 13/106,906

(22) Filed: May 13, 2011

(65) Prior Publication Data

US 2011/0288227 A1 Nov. 24, 2011

Related U.S. Application Data

(60) Provisional application No. 61/345,624, filed on May 18, 2010.

(51) Int. Cl.
*B01J 19/06* (2006.01)
*C08F 222/40* (2006.01)
*C08F 220/56* (2006.01)

(52) U.S. Cl. .......................... 524/516; 524/548; 524/547

(58) Field of Classification Search .................. 524/516, 524/548, 547
See application file for complete search history.

(56) References Cited

U.S. PATENT DOCUMENTS

| | | | |
|---|---|---|---|
| 4,049,705 A | 9/1977 | Schwing | |
| 4,262,072 A | 4/1981 | Wendling et al. | |
| 4,503,169 A | 3/1985 | Randklev | |
| 4,619,979 A | 10/1986 | Kotnour et al. | |
| 4,843,134 A | 6/1989 | Kotnour et al. | |
| 5,637,646 A | 6/1997 | Ellis | |
| 5,804,610 A | 9/1998 | Hamer et al. | |
| 7,090,721 B2 | 8/2006 | Craig et al. | |
| 7,090,722 B2 | 8/2006 | Budd et al. | |
| 7,156,911 B2 | 1/2007 | Kangas et al. | |
| 7,452,924 B2 | 11/2008 | Aasen et al. | |
| 7,649,029 B2 | 1/2010 | Kolb et al. | |
| 7,674,850 B2 | 3/2010 | Karim et al. | |
| 2004/0054041 A1 | 3/2004 | Schmidt | |
| 2009/0060859 A1 | 3/2009 | Garcia Castro et al. | |

FOREIGN PATENT DOCUMENTS

| | | |
|---|---|---|
| DE | 2750030 | 5/1979 |
| JP | 2009149828 | 7/2009 |
| JP | 2009179727 | 8/2009 |
| WO | WO 2006/053083 | 5/2006 |
| WO | WO 2006/053083 A2 * | 5/2006 |
| WO | WO 2011/025847 | 3/2011 |

OTHER PUBLICATIONS

PCT International Search Report, PCT/US2011/036370.
Ohno, et al., "Development of new class of ion conductive polymers based on ionic liquids," Electrochimica Acta, vol. 50, pp. 255-261, 2004.
Zaderenko, et al., "Synthesis and Regioselective Hydrolysis of 2-Imidazol-1-ylsuccinic Esters," Journal of Organic Chemistry, vol. 59, Issue 21, pp. 6268-6273, (1994).
Klee et al., "Monomers for low shrinking composites, $2^a$—Synthesis of branched methacrylates and their application in dental composites," Macromolecular Chemistry and Physics, vol. 200, Issue 3, pp. 517-523, (1999).

* cited by examiner

*Primary Examiner* — William Cheung
(74) *Attorney, Agent, or Firm* — Kent S. Kokko

(57) ABSTRACT

The compositions comprise an acid functional monomer or acid-functional copolymer (or conjugate base thereof), and an imidazole compound (or conjugate acid thereof).

18 Claims, No Drawings

POLYMERIZABLE IONIC LIQUID COMPOSITIONS

CROSS REFERENCE TO RELATED APPLICATION

This application claims the benefit of U.S. Provisional Patent Application No. 61/345,624, filed May 18, 2010, the disclosure of which is incorporated by reference herein in its entirety.

FIELD OF THE INVENTION

The present disclosure is directed to novel polymerizable ionic liquid compositions, and uses thereof.

BACKGROUND

Ionic liquids (ILs) are salts in which the cation and anion are poorly coordinated. At least one of the ionic components is organic and one of the ions has a delocalized charge. This prevents the formation of a stable crystal lattice, and results in such materials existing as liquids, often at room temperature, and at least, by definition, at less than 100° C. For example, sodium chloride, a typical ionic salt, has a melting point of about 800° C., whereas the ionic liquid N-methylimidazolium chloride has a melting point of about 75° C.

Ionic liquids typically comprise an organic cation, such as a substituted ammonium or a nitrogen-containing heterocycle, such as a substituted imidazolium, coupled with an inorganic anion. However, species have also been described wherein the cation and anion are organic. When the ionic liquid comprises at least one polymerizable group, it is a polymerizable ionic liquid ("PIL").

Some of the features of ionic liquids that have caused the considerable research and development efforts in recent years include a broad liquid range and their high dissolving power—ionic liquids are excellent solvents for both organic and inorganic materials. Additionally, ionic liquids have high polarity, high thermal stability, high refractive indices, and high ionic conductivity. They are also non-flammable and have negligible vapor pressure. As a reaction medium, ionic liquids have been shown to accelerate many organic reactions including Diels-Alder cycloaddition reactions and alkylation reactions.

The combination of polymerizable functionality, room temperature organic liquid salt characteristics, high refractive index, high ionic conductivity, and negligible vapor pressure may enable their incorporation into new high value functional materials. Because of their low volatility, non-flammability, high solvency attributes, and potential ability to be recycled, ionic liquids have been promoted as environmentally safe or "green" solvents to replace conventional organic solvents (volatile organic compounds, VOCs).

SUMMARY

The present disclosure provides polymerizable ionic liquid compositions that are useful in a variety of adhesive and coating applications. The compositions comprise an acid functional monomer or acid-functional copolymer (or conjugate base thereof), and an imidazole compound of formula I (or conjugate acid thereof). The composition is formed by acid-base interactions between the acid groups of the monomer and the imidazole compound, and by free radical polymerization of the ionic liquid monomer.

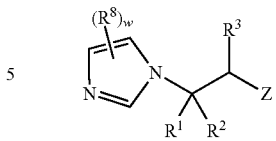

wherein
Z comprises a ketone, ester, amide, nitrile, or azlactone functional group,
$R^1$ is H or a $C_1$-$C_{25}$ alkyl group,
$R^2$ is H, a $C_1$-$C_{25}$ alkyl group or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and
$R^3$ is H or $CH_3$, preferably H;
$R^8$ is a (hetero)hydrocarbyl group which may be substituted at the 2-, 4 or 5-position, and w is 0, 1, 2 or 3;
with the proviso that when Z comprises nitrile or azlactone functional group, then $R^1$ and $R^2$ are H.

In embodiments of Formula I where Z is an azlactone functional group, Z is of the formula:

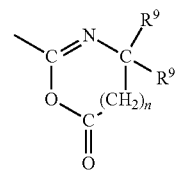

where each $R^9$ is independently H, an alkyl group having 1 to 14 carbon atoms, and n is 0 or 1.

In other embodiments where Z comprises an ester, amide or ketone functional group Z is of the formula —C(O)—($X^1$)$_a$—$R^{10}$, where $R^{10}$ is a (hetero)hydrocarbyl group, said (hetero)hydrocarbyl optionally substituted with one or more hydroxyl groups, and $X^1$ is —O— or —$NR^6$—, where $R^6$ is H or a $C_1$-$C_6$ alkyl, and a is 0 or 1. Preferably $R^{10}$ is a hydrocarbyl group, and more preferably $R^{10}$ is an alkyl group of 1 to 25 carbon atoms. $R^{10}$ is optionally substituted with a hydroxyl groups.

In one embodiment, the composition is a polymerizable ionic liquid comprising a polymerizable anion and a cation corresponding to the conjugate acid of the imidazole compound of Formula I. Such polymerizable compositions may further comprise an initiator and can provide an air to nitrogen curing exotherm ratio of at least 0.70. When the multifunctional polymerizable ionic liquid has a sufficiently high air to nitrogen curing exotherm ratio, the polymerizable ionic liquid can be cured in air, rather than requiring curing in the absence of oxygen such as by curing in the presence of nitrogen.

In another embodiment this disclosure provides a crosslinkable composition comprising an acid-functional copolymer and a compound of Formula I. Such compositions may comprise a syrup polymer composition comprising a solute acid functional copolymer, a solvent acid functional monomer and the imidazole compounds of Formula I, which form an acid-base interaction between the imidazole group(s) and the acid groups of the acid functional copolymer.

As used herein:
"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"poly(meth)acryloyl" means a compound having two or more (meth)acryloyl groups that may function as Michael acceptors.

"curable" means that a coatable material can be transformed into a solid, substantially non-flowing material by means of cooling (to solidity hot melts), heating (to dry and solidify materials in a solvent), chemical cross linking, radiation crosslinking, or the like.

"alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

"aryl" is an aromatic group containing 6-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

"(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

The imidazole compounds of Formula I are Michael addition products of an imidazole compound and a Michael acceptor compound; i.e. a compound having an electron deficient double bond, and an electron-withdrawing functional group, including α,β-unsaturated esters, amides, ketones, nitriles and azlactones. Such compounds may be prepared as described in Scheme I.

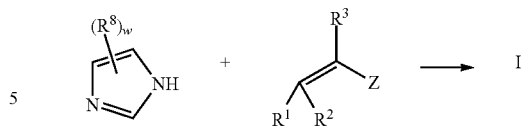

Where
Z comprises a ketone, ester, amide, nitrile, or azlactone functional group,
$R^1$ is H or a $C_1$-$C_{25}$ alkyl group,
$R^2$ is H or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and
$R^3$ is H or $CH_3$,
$R^8$ is a (hetero)hydrocarbyl group, including alkyl and aryl, preferably an alkyl group, and w is 0, 1, 2 or 3;

In some embodiments, the imidazole compounds may be prepared by the Michael addition reaction of an imidazole compound to a poly(meth)acryloyl compound as illustrated in Scheme II:

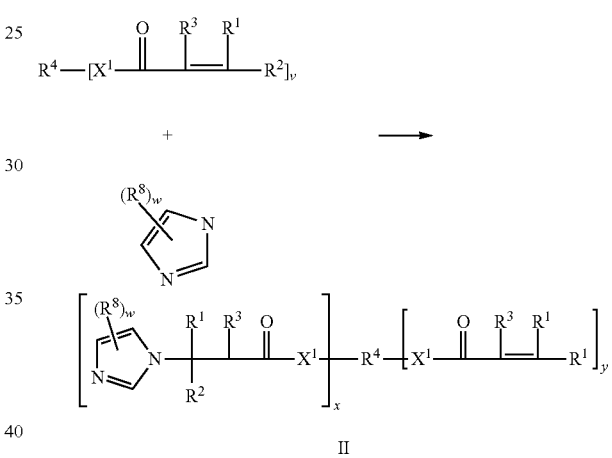

II where
$R^1$ is H or a $C_1$-$C_{25}$ alkyl group,
$R^2$ is H or —CO—$X^1$—$R^5$, where $R^5$ is a H or a $C_1$-$C_{25}$ alkyl group and $X^1$ is —O— or —$NR^6$—,
where $R^6$ is H or a $C_1$-$C_6$ alkyl; and
$R^3$ is H or $CH_3$,
$R^4$ is a (hetero)hydrocarbyl linking groups that may further comprise one of more catenary (in-chain) functional groups, including ester, amide, urethane and other functional groups, and is preferably a hydrocarbyl group including alkylene, cycloalkylene, or combinations thereof, optionally substituted with one or more hydroxyl groups;
$R^8$ is a (hetero)hydrocarbyl group, and w is 0, 1, 2 or 3;
$X^1$ is —O— or —$NR^6$—, where $R^6$ is H or a $C_1$-$C_6$ alkyl;
x is 1 to 6, preferably 1 to 4,
y is 0 to 2, and
v is x+y.

As can be seen, the compounds of Formula II in Scheme II may have two or more imidazole groups, enabling crosslinking of acid-functional copolymers by acid-base interaction. Further, compounds of Formula II may be provided having a (meth)acryloyl group which may be subsequently polymerized by free radical means to crosslink the composition. Compositions including compounds of Formula II may be combined with other monomer or acid-functional copolymers, as will be described further.

As illustrated supra, the compounds of Formula II may be prepared by Michael addition of an imidazole compound to a polyacryloyl compound. Useful polyacryloyl compounds include those of the general formula:

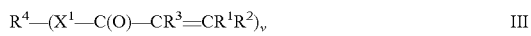

wherein each $X^1$ is selected from alkylene, —O—, or —$NR^6$— where each $R^6$ independently represents H or an alkyl group having from 1 to 6 carbon atoms;

$R^4$ is a (hetero)hydrocarbyl linking groups that may further comprise one of more catenary (in-chain) functional groups, including ester, amide, urethane and other functional groups, and is preferably a hydrocarbyl group including alkylene, cycloalkylene, or combinations thereof, optionally substituted with one or more hydroxyl groups;

v is greater than 1, preferably greater than or equal to 2 and is generally 2 to 6.

In one embodiment, $R^4$ may be a polyvalent organic group having a valence of at least 2. Examples of polyvalent groups $R^4$ include butylene; ethylene; propylene; and 4-oxaheptalene; hexylene; and 1,4-bis(methyl)cyclohexylene. All isomers or the alkylene groups are envisioned, such a 1,2-, 1,3- and 1,4-butylene isomers. The alkylene may be further substituted with a hydroxyl group, e.g. 2-hydroxy-1,3-propylene.

Useful polyacryl compounds include, for example, acrylate monomers selected from the group consisting of (a) diacryl containing compounds such as ethylene glycol diacrylate, 1,3-butylene glycol diacrylate, 1,4-butanediol diacrylate, 1,6-hexanediol diacrylate, cyclohexane dimethanol diacrylate, alkoxylated hexanediol diacrylate, neopentyl glycol diacrylate, caprolactone modified neopentylglycol hydroxypivalate diacrylate, cyclohexanedimethanol diacrylate, diethylene glycol diacrylate, dipropylene glycol diacrylate, bisphenol-A diacrylate, ethoxylated bisphenol-A diacrylate, hydroxypivalaldehyde modified trimethylolpropane diacrylate, neopentyl glycol diacrylate, polyethylene glycol diacrylate, propoxylated neopentyl glycol diacrylate, tetraethylene glycol diacrylate, tricyclodecanedimethanol diacrylate, triethylene glycol diacrylate, tripropylene glycol diacrylate; (b) triacryl containing compounds such as glycerol triacrylate, ethoxylated triacrylates (e.g., ethoxylated trimethylolpropane triacrylate, pentaerythritol triacrylate, propoxylated triacrylates (e.g., propoxylated glyceryl triacrylate, propoxylated trimethylolpropane triacrylate, tris(2-hydroxyethyl)isocyanurate triacrylate; (c) higher functionality acryl-containing compounds such as ditrimethylolpropane tetraacrylate, dipentaerythritol pentaacrylate, ethoxylated pentaerythritol tetraacrylate, pentaerythritol tetraacrylate, caprolactone modified dipentaerythritol hexaacrylate; (d) oligomeric acryl compounds such as, for example, urethane acrylates, polyester acrylates, epoxy acrylates; polyacrylamide analogues of the foregoing; and combinations thereof.

Such compounds are available from vendors such as Sartomer Company, Exton, Pa.; UCB Chemicals Corporation, Smyrna, Ga.; and Aldrich Chemical Company, Milwaukee, Wis. Additional useful acrylate materials include hydantoin moiety-containing polyacrylates, for example, as described in U.S. Pat. No. 4,262,072 (Wendling et al.).

Other useful polyacryl compounds also include, for example, free-radically polymerizable acrylate oligomers and polymers having pendant (meth)acryl groups wherein at least two of the (meth)acryl groups are acryl groups. There is a differential reactivity between acryl and methacryl groups with respect to Michael-type addition. Michael-type addition typically occurs easily with acryl groups, but may occur only with difficulty if at all, in the case of methacryl groups. For this reason, the polyacryl component typically has at least two acryl group (e.g., as part of acryloxy or acrylamido functionality), although the poly(meth)acryl compound may also have additional (meth)acryl groups (e.g., as part of methacrylate or methacrylamido functionality). Advantageously, composition may be prepared in which Michael addition occurs through the acryl groups, leaving methacryl groups unreacted. Such unreacted methacryl groups may be subsequently free-radically polymerized.

With respect to the useful polyacryl compounds presented above, it will be understood that the corresponding amides or thioesters are also useful. The multifunctional ethylenically unsaturated monomer is preferably an ester of acrylic acid. It is more preferably selected from the group consisting of a difunctional ethylenically unsaturated ester of acrylic, a trifunctional ethylenically unsaturated ester of acrylic, a tetrafunctional ethylenically unsaturated ester of acrylic, and a combination thereof. Of these, difunctional and trifunctional ethylenically unsaturated esters of acrylic acid are more preferred.

Other useful acrylate oligomers include acrylated epoxies, for example, diacrylated esters of epoxy-functional materials (e.g., diacrylated esters of bisphenol A epoxy-functional material) and acrylated urethanes. Useful acrylated epoxies include, for example, acrylated epoxies available under the trade designations "EBECRYL 3500", "EBECRYL 3600", "EBECRYL 3700", and "EBECRYL 3720" from UCB Chemicals Corporation. Useful acrylated urethanes include, for example, acrylated urethanes available under the trade designations "EBECRYL 270", "EBECRYL 1290", "EBECRYL 8301", and "EBECRYL 8804" from UCB Chemicals Corporation.

The multifunctional ethylenically unsaturated monomer is preferably an ester of acrylic acid. It is more preferably selected from the group consisting of a difunctional ethylenically unsaturated ester of acrylic, a trifunctional ethylenically unsaturated ester of acrylic, a tetrafunctional ethylenically unsaturated ester of acrylic, and a combination thereof. Of these, difunctional and trifunctional ethylenically unsaturated esters of acrylic acid are more preferred.

Preferred multifunctional ethylenically unsaturated esters of acrylic acid and can be described by the formula:

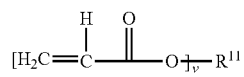

$R^{11}$ is an alkylene, cycloalkylene, or combinations thereof, optionally substituted with a hydroxyl group, generally $R^{10}$ is the residue of a polyol;

v is greater than 1, preferably greater than or equal to 2 and is generally 2 to 6.

Examples of suitable multifunctional ethylenically unsaturated esters of acrylic acid are the polyacrylic acid or polymethacrylic acid esters of polyhydric alcohols including, for example, the diacrylic acid and dimethylacrylic acid ester of aliphatic diols such as ethyleneglycol, triethyleneglycol, 2,2-dimethyl-1,3-propanediol, 1,3-cyclopentanediol, 1-ethoxy-2,3-propanediol, 2-methyl-2,4-pentanediol, 1,4-cyclohexanediol, 1,6-hexamethylenediol, 1,2-cyclohexanediol, 1,6-cyclohexanedimethanol; the triacrylic acid esters of aliphatic triols such as glycerin, 1,2,3-propanetrimethanol, 1,2,4-butanetriol, 1,2,5-pentanetriol, 1,3,6-hexanetriol, and 1,5,10-decanetriol; the triacrylic acid acid esters of tris(hydroxyethyl) isocyanurate; the tetraacrylic acid esters of aliphatic triols, such as 1,2,3,4-butanetetrol, 1,1,2,2-tetramethylolethane, 1,1,3,3-tetramethylolpropane, and pentaerythritol tetraacrylate; the pentaacrylic acid and pentamethacrylic acid esters of aliphatic pentols such as adonitol; the hexaacrylic acid acid esters of hexanols such as sorbitol and dipentaerythritol; the di acrylic acid acid esters of aromatic diols such as resorcinol, pyrocatechol, bisphenol A, and bis(2-hydroxyethyl) phthalate; the triacrylic acid ester of aromatic triols such as pyrogallol, phloroglucinol, and 2-phenyl-2,2-methylolethanol; and the hexaacrylic acid esters of dihydroxy ethyl hydantoin; and mixtures thereof.

The compounds of Formulas II function as reactive monomers and thus are substantially unpolymerized in the curable composition at the time the curable composition is applied to a substrate or formed into a (e.g. dental) article, such as a dental crown. Hence, the curable composition hardens upon curing via polymerization of the ethylenically unsaturated groups of the (e.g. multifunctional) polymerizable ionic liquid. Such curing generally results in a permanent bond. For example, when the curable composition is an adhesive, the bonded substrate typically cannot be separated without substrate damage.

In some favored embodiments, the compounds of Formulas II and IV are sufficiently low in viscosity that they act as a reactive diluent. In such embodiment, the composition can advantageously be substantially free of solvents, especially organic solvents. This can result in increased efficiency with respect to manufacturing time as well as energy consumption by reducing or eliminating drying the composition prior to curing. This can also reduce the volatile organic content (VOC) emissions of the composition.

Compounds of Formula I, where Z is an azlactone functional group may be prepared by Michael addition of an imidazole compound to a azlactone compound as shown in Scheme III:

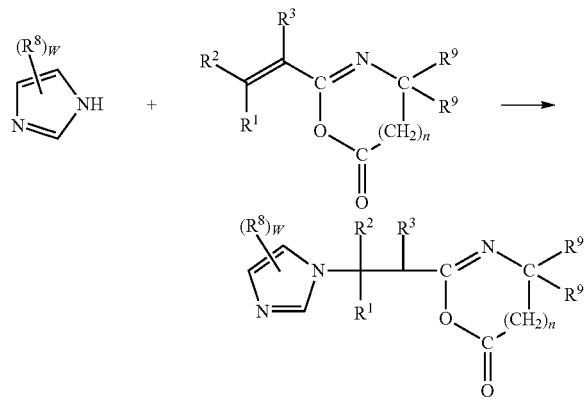

where
$R^1$ and $R^2$ are H; and
$R^3$ is H or $CH_3$,
$R^8$ is a (hetero)hydrocarbyl group, including alkyl and aryl, preferably an alkyl group, and w is 0, 1, 2 or 3;
each $R^9$ is independently H, an alkyl group having 1 to 14 carbon atoms, and n is 0 or 1.

The anionic monomers of the polymerizable ionic liquid have an ethylenically unsaturated polymerizable groups and an acid group. The acid functional group may be an acid per se, such as a carboxylic acid, or a portion may be the conjugate base thereof. In the presence of the imidazole compound, these acid functional monomers form the conjugate base.

Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. Depending on the desired end use and physical properties of the final composition, the acid functional monomer may used in amounts of 5 molar equivalents or more relative to the molar equivalents of the imidazole groups. In some embodiments the molar ratio of acid groups to imidazole groups is approximately equimolar ±20%.

Preferred polymerizable ionic liquids exhibit a high air to nitrogen curing exotherm ratio, as can be measured by photo DSC according to the test method described in the examples. The air to nitrogen curing ratio is typically at least 0.70. In preferred embodiments, the air to nitrogen curing exotherm ratio is typically at least the 0.80 and preferably at least 0.90. For embodiments wherein the air to nitrogen curing ratio of the polymerizable ionic liquid is sufficiently high, the polymerizable ionic liquid can advantageously be substantially completely cured in air (i.e. an oxygen rich environment) rather than requiring curing in the absence of oxygen.

In some embodiments, a completely cured (i.e. hardened) polymerizable ionic liquid is solid at 25° C. In other embodiments, particularly where low Tg optional monomers are used, the completely cured polymerizable ionic liquid may be a liquid at 25° C. In some embodiments the hardened composition is substantially free of uncured polymerizable ionic liquid, i.e. <10% extractable. When significant uncured polymerizable ionic liquid is present it typically results as a surface residue exhibiting a "wet" appearance. Minimal surface inhibition not only provides more complete curing but also minimizes the formation of a less cured oxygen inhibited surface layer. This provides the benefit of reduced extractables and also less need to remove the uncured "wet" monomer layer by use of an absorbent wiping material with or without a solvent such as ethanol. The extent of curing can be determined by various methods known in art. One common method is to determine the amount of uncured material by solvent extraction. In preferred embodiments, the amount of uncured extractable polymerizable ionic liquid is less than 10%, more preferably less than 5%, and most preferably less than 1% by weight of the cured composition.

The polymerizable ionic liquid may also comprise other conventional (e.g. (meth)acrylate) ethylenically unsaturated monomer(s), oligomer(s), or polymer(s). By "optional monomers" is it meant an ethylenically unsaturated monomer that is not a polymerizable ionic liquid, and includes polar and nonpolar monomers and oligomers, as described more fully herein. Although conventional monomers are polymerizable and many are liquids at 25° C., conventional monomers are typically non-ionic, lacking a cation and an anion.

Conventional (meth)acrylate monomers typically have an air to nitrogen curing exotherm ratio of no greater than 0.50, 0.40, 0.35, 0.20, or 0.25 or lower. For example, triethylene glycol dimethacrylate (TEGMA) has been found to have an air to nitrogen curing exotherm ratio of about 0.36; whereas hydroxyethyl methacrylate (HEMA) has been found to have an air to nitrogen curing exotherm ratio of less than 0.25. Although the photocuring of conventional (meth)acrylate monomers and especially methacrylate monomers is typically inhibited by oxygen present in air, the inclusion of the (e.g. multifunctional) polymerizable ionic liquid can sufficiently increase the air to nitrogen curing exotherm of the mixture such that the mixture can advantageously be substantially completely cured in air. For embodiments wherein the composition is to be cured in air and the multifunctional polymerizable ionic liquid is combined with the "optional" polymerizable (meth)acrylate monomer, which exhibits a lower air to nitrogen curing exotherm ratio, the air to oxygen curing exotherm ratio of the (e.g. multifunctional) polymerizable ionic liquid, described herein, is at least 0.85, preferably at least 0.90, and more preferably at least 0.95.

The total concentration of polymerizable ionic liquid(s) having a high air to nitrogen curing exotherm ratio, is typically at least 30 wt-% and preferably at least 40 wt-% of the unfilled composition (the total polymerizable organic composition excluding inorganic filler). In this embodiment, the total concentration of other ethylenically unsaturated (e.g. (meth)acrylate) monomer(s), oligomer(s), and polymer(s)) is typically at least 10 wt-%, 20 wt-%, 30 wt-%, 40 wt-%, 50 wt-%, or 65 wt-%.

In many embodiments, it is preferred to maximize the concentration of other ethylenically unsaturated (e.g. (meth) acrylate) monomer(s), oligomer(s) provided that the air to oxygen curing ratio of the mixture is at least 0.75 and preferably at least 0.80, 0.85, 0.90 or greater.

The polymerizable ionic liquid composition may further comprise (meth)acrylate ester monomers as an "optional" monomer. The (meth)acrylate ester monomer useful in preparing the acid functional (meth)acrylate adhesive copolymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth) acrylate ester monomer is the ester of (meth)acrylic acid with an alcohol derived from a renewable source, such as 2-octanol, citronellol, dihydrocitronellol.

In some embodiments it is desirable for the (meth)acrylic acid ester monomer to include a high $T_g$ monomer, have a $T_g$ of at least 25° C., and preferably at least 50° C. Suitable high Tg monomers include Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of 85 to 99.5 parts by weight based on 100 parts total "optional" monomer content used to prepare the polymer. Preferably (meth)acrylate ester monomer is present in an amount of 90 to 95 parts by weight based on 100 parts total monomer content. When high Tg monomers are included, the copolymer may include up to 30 parts by weight, preferably up to 20 parts by weight of the 85 to 99.5 parts by weight of (meth)acrylate ester monomer component.

The polymerizable ionic liquid may further comprise polar monomers as an optional "other monomer". The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 0.5 to 5 parts by weight, based on 100 parts by weight "optional" monomer.

The polymerizable ionic liquid may further comprise vinyl monomers as the optional "optional" monomer, and includes vinyl esters (e.g., vinyl acetate and vinyl propionate), styrene, substituted styrene (e.g., α-methyl styrene), vinyl halide, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight "optional" monomer.

The polymerizable ionic liquid may further comprise a multifunctional poly(meth)acryloyl monomer incorporated into the blend of polymerizable monomers as a component of the "optional" monomers. Multifunctional acrylates are particularly useful for emulsion or UV polymerization. Examples of useful multifunctional (meth)acrylate include, but are not limited to, di(meth)acrylates, tri(meth)acrylates, and tetra(meth)acrylates, such as 1,6-hexanediol di(meth) acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth) acrylate is tailored depending upon the particular application.

Typically, the multifunctional (meth)acrylate is present in amounts less than 5 parts based on total dry weight of adhesive composition. More specifically, the crosslinker may be present in amounts from 0.01 to 50 parts, preferably 0.05 to 20 parts, most preferably 0.05 to 1 parts, based on 100 parts "optional" monomers of the adhesive composition.

In such embodiments, the "optional" monomer component may comprise:
i. 85 to 99.5 parts by weight of an (meth)acrylic acid ester monomers;
ii. 0.5 to 15 parts by weight of an acid functional ethylenically unsaturated monomer;
iii. 0 to 10 parts by weight of a non-acid functional, ethylenically unsaturated polar monomer;
iv. 0 to 5 parts vinyl monomer; and
v. 0 to 50 parts of a multifunctional (meth)acrylate;
based on 100 parts by weight total "optional" monomer.

Some portion of the (meth)acrylic acid ester monomer units may be hydrolyzed after the copolymer is prepared.

In some embodiments the composition may include filler. Such compositions may include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such compositions comprising appreciable amounts of filler, the one or more polymerizable ionic liquids are typically present in an amount totaling at least 5 wt-%, preferably at least 10 wt-%, based on the total weight of the composition. The concentration of multifunctional polymerizable ionic liquids is generally no greater than about 60 wt-%. In some embodiments the total amount of multifunctional polymerizable ionic liquids is at most 40 wt-%, preferably at most 30 wt-%, and more preferably at most 25 wt-%.

Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

In some embodiments, the composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art.

The polymerizable mixture comprising the ionic polymerizable liquid and "optional" monomers may be polymerized by any conventional free radical polymerization method, including solution, radiation, bulk, dispersion, emulsion, and suspension processes. For optical applications, solution, UV and bulk processes are preferred. The resulting (co)polymers may be random or block (co)polymers.

Initiators useful in preparing the (meth)acrylate adhesive copolymers used in the present invention are initiators that, on exposure to heat, generate free-radicals which initiate (co) polymerization of the monomer mixture. Water-soluble initiators are preferred for preparing the (meth)acrylate polymers by emulsion polymerization. Suitable water-soluble initiators include but are not limited to those selected from the group consisting of potassium persulfate, ammonium persulfate, sodium persulfate, and mixtures thereof; oxidation-reduction initiators such as the reaction product of the above-mentioned persulfates and reducing agents such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include but are not limited to those selected from the group consisting of azo compounds such as VAZO™ 64 (2,2'-azobis(isobutyronitrile)) and VAZO™ 52 (2,2'-azobis(2,4-dimethylpentanenitrile)), both available from E.I. du Pont de Nemours Co., peroxides such as benzoyl peroxide and lauroyl peroxide, and mixtures thereof. The preferred oil-soluble thermal initiator is (2,2'-azobis(isobutyronitrile)). When used, initiators may comprise from about 0.05 to about 1 part by weight, preferably about 0.1 to about 0.5 part by weight based on 100 parts by weight of monomer components in the pressure-sensitive adhesive.

Alternatively, the mixture can be polymerized by techniques including, but not limited to, the conventional techniques of solvent polymerization, dispersion polymerization, and solventless bulk polymerization. The monomer mixture may comprise a polymerization initiator, especially a thermal initiator or a photoinitiator of a type and in an amount effective to polymerize the comonomers, as previously described.

A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and an ethylene glycol alkyl ether. Those solvents can be used alone or as mixtures thereof.

In a typical photopolymerization method, a monomer mixture may be irradiated with ultraviolet (UV) rays in the presence of a photopolymerization initiator (i.e., photoinitiators). Preferred photoinitiators are those available under the trade designations IRGACURE™ and DAROCUR™ from Ciba Speciality Chemical Corp., Tarrytown, N.Y. and include 1-hydroxy cyclohexyl phenyl ketone (IRGACURE™ 184), 2,2-dimethoxy-1,2-diphenylethan-1-one (IRGACURE 651), bis(2,4,6-trimethylbenzoyl)phenylphosphineoxide (IRGACURE™ 819), 1-[4-(2-hydroxyethoxy)phenyl]-2-hydroxy-2-methyl-1-propane-1-one (IRGACURE™ 2959), 2-benzyl-2-dimethylamino-1-(4-morpholinophenyl)butanone (IRGACURE™ 369), 2-methyl-1-[4-(methylthio)phenyl]-2-morpholinopropan-1-one (IRGACURE™ 907), and 2-hydroxy-2-methyl-1-phenyl propan-1-one (DAROCUR™ 1173). Particularly preferred photoinitiators are IRGACURE™ 819, 651, 184 and 2959.

Solventless polymerization methods, such as the continuous free radical polymerization method described in U.S. Pat. Nos. 4,619,979 and 4,843,134 (Kotnour et al.), the essentially adiabatic polymerization methods using a batch reactor described in U.S. Pat. No. 5,637,646 (Ellis), and, the methods described for polymerizing packaged pre-adhesive compositions described in U.S. Pat. No. 5,804,610 (Hamer et al.) may also be utilized to prepare the polymers.

As an alternative to adding the polymerizable ionic liquid to the "optional" monomers, and then polymerizing, the imidazole compound of Formulas I or II may be added to a separately prepared, extant acid-functional copolymer comprising the acid functional and "optional" monomers described supra. It is believed that the amino groups of the imidazole compound of Formulas I and II interact with the pendent acid functional groups of the acid functional (meth) acrylate copolymer to form an ionic linkage, i.e. an imidazolium group. In embodiments where the imidazole compound has two or more imidazole groups, the polymer compositions can crosslink by forming a plurality of ionic bonds between the polymer chains. In composition comprising the compounds of Formula II, having (meth)acryloyl groups, may also crosslink the polymer by free radical polymerization.

The copolymerizable mixture may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The polymerizable mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

In embodiments where the imidazole compound further comprises pendent (meth)acrylate polymerizable groups, as in Formula II, the pendent (meth)acrylate group may be subsequently free radically polymerized to crosslink the copolymer.

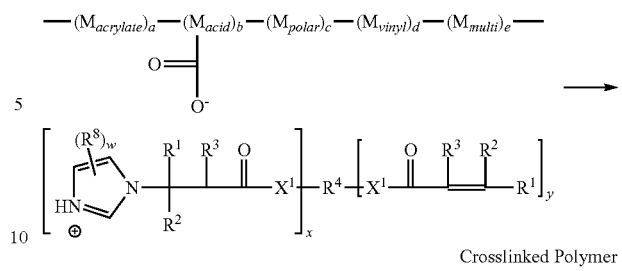

Crosslinked Polymer where $M_{acrylate}$ represents polymerized (meth)acrylate monomer units derived from (meth)acrylic acid ester of non-tertiary alcohol having "a" polymerized monomer units, $M_{acid}$ represents polymerized monomer units derived from acid functional monomers having "b" polymerized monomer units, shown as the conjugate base although the acid may be present;

$M_{polar}$ represents polymerized polar monomer units having "c" polymerized monomer units, $M_{vinyl}$ represents polymerized vinyl monomer units derived from acid functional monomers having "d" polymerized monomer units, and $M_{multi}$ represents polymerized multifunctional (meth)acrylate monomer units having "e" polymerized monomer units, and wherein a and b are at least one and c, d, and e may be zero or non-zero, and $R^1$ is H or a $C_1$-$C_{25}$ alkyl group, $R^2$ is H or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and $R^3$ is H or $CH_3$, $R^4$ is a (hetero)hydrocarbyl linking groups that may further comprise one of more catenary (in-chain) functional groups, including ester, amide, urethane and other functional groups, and is preferably a hydrocarbyl group including alkylene, cycloalkylene, or combinations thereof, optionally substituted with one or more hydroxyl groups;

$R^8$ is a (hetero)hydrocarbyl group, including alkyl and aryl, preferably an alkyl group, and w is 0, 1, 2 or 3;

$X^1$ is —O— or —$NR^6$—, where $R^6$ is H or a $C_1$-$C_6$ alkyl;

x is 1 to 6, preferably 1 to 4;

y is 0 to 5, preferably 0 to 2.

It will be understood that the values of subscripts a to e correspond to the amounts of the "optional" monomers in the polymerizable composition, i.e. 85 to 99.5 parts by weight of an (meth)acrylic acid ester monomer; and 0.5 to 15 parts by weight of an acid functional monomer. Other monomers may be present in the amounts previously recited.

The curable blends of polymerizable ionic liquid in combination with the "other monomers" (e.g. (meth)acrylate) ethylenically unsaturated monomers can be used for a variety of other uses, particularly (e.g. photo) curable coatings. A coated article can be prepared by applying the composition described herein to a substrate and curing the composition.

The curable composition can be applied to a variety of substrates. Suitable substrate materials include inorganic substrates such as glass or ceramics, natural and synthetic organic substrates such as paper, wood, as well as thermosetting or thermoplastic polymers such as polycarbonate, poly (meth)acrylate (e.g., polymethyl methacrylate or "PMMA"), polyolefins (e.g., polypropylene or "PP"), polyurethane, polyesters (e.g., polyethylene terephthalate or "PET"), polyamides, polyimides, phenolic resins, cellulose diacetate, cellulose triacetate, polystyrene, styrene-acrylonitrile copolymers, epoxies, and the like. The substrate thickness typically also will depend on the intended use. For most applications, substrate thicknesses of less than about 0.5 mm are preferred, and more preferably about 0.02 to about 0.2 mm. The substrate can be treated to improve adhesion between the substrate and curable coating compositions, e.g., chemical treatment, corona treatment such as air or nitrogen corona, plasma, flame, or actinic radiation. If desired, an optional tie layer or (e.g. polymerizable ionic liquid based) primer can be applied to the substrate to increase the interlayer adhesion.

The curable coating composition can be applied using a variety of conventional coating methods. Suitable coating methods include, for example, spin coating, knife coating, die coating, wire coating, flood coating, padding, spraying, roll coating, dipping, brushing, foam application, and the like. The coating is dried, typically using a forced air oven. The dried coating is at least partially and typically completely cured using an energy source.

The polymerizable ionic liquid composition of this disclosure provides a pre-adhesive, curable syrup copolymer composition comprising the imidazole compounds of Formulas I or II, and a polymerizable anionic monomer, which when polymerized provides a pressure-sensitive adhesive composition. The adhesive may comprise up to 100% by weight of the polymerized ionic liquid compositions The pre-adhesive composition may further comprise the "optional" monomers previous described.

Alternatively, the present disclosure provides an adhesive composition comprising the imidazole compound of Formulas I and II and an acid-functional (meth)acrylate solute copolymer. In some embodiments the composition crosslinks by acid-base interactions between the acid groups of the copolymer and the nitrogen atoms of the imidazole compound.

In this application "pre-adhesive" refers to the syrup composition comprising an acid-functional (meth)acrylate solute copolymer, and an aminoalkyl (meth)acryloyl solvent monomer which may be crosslinked to form a pressure-sensitive adhesive. "Syrup polymer" refers to a solution of a solute polymer in one or more solvent monomers, the solution having a viscosity of from 500 to 10,000 cPs at 22° C.

The pressure-sensitive adhesives of this disclosure, i.e. the crosslinked compositions, provide the desired balance of tack, peel adhesion, and shear holding power, and further conform to the Dahlquist criteria; i.e. the modulus of the adhesive at the application temperature, typically room temperature, is less than $3 \times 10^6$ dynes/cm at a frequency of 1 Hz.

The polymerizable ionic liquid composition provides curable dental compositions. The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. Dental adhesives are also hardened by curing after applying the dental composition to the tooth. The method of treating an oral surface may comprise providing a dental article and adhering the dental article to an oral (e.g. tooth) surface. The dental article may comprise a cured composition comprising a polymerizable ionic liquid as described herein. Alternatively, the dental article may be a conventional dental article (without a polymerizable ionic liquid) adhered with a conventional primer (without a polymerizable ionic liquid) and an adhesive comprising a polymerizable ionic liquid; a primer comprising a polymerizable ionic liquid and a conventional adhesive (without a polymerizable ionic liquid); or both a primer and adhesive, each comprising a polymerizable ionic liquid.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill bland and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

The polymerizable ionic liquid compositions may also be used in the preparation of antistatic coatings. Some advantages used include that the antistatic coatings disclosed herein (1) adhere well to a variety of optical films; (2) impart good antistatic properties to the resultant optical device; (3) can be durable so as to withstand handling and manipulation as the optical device is used, e.g., to manufacture a display device; and (4) are clear and colorless, making them well suited for various light management purposes as they can be used as is or have additional agents imparted therein to provide color selection, haze, or other desired effect. Useful antistatic coatings have a conductivity of $<5 \times 10^{13}$ ohm/square. Mono-imidazole compounds of formula I are most useful in preparing antistatic coatings.

Generally, curable systems containing a significant amount of solvent, monomers and reactive diluents can give rise to a significant increase in density when transformed from the uncured to the cured state causing a net shrinkage in volume. As is well known, shrinkage can cause unpredictable registration in precise molding operations such as those required in dental applications. Shrinkage can also create residual stress in such articles, which can subsequently lead to stress cracking.

In some embodiments, compositions of this disclosure minimizes shrinkage and stress cracking. The low shrinkage compositions of this invention are particularly useful in molding applications or in any applications where accurate molding and/or registration is required. In some embodiments the present disclosure provides compositions that exhibit less than 10% shrinkage, and preferably less than 8%. The compositions are low in viscosity and suitable for molding processes, including precision molding processes.

MATERIALS

Reagents used were obtained from Sigma-Aldrich Chemical Company, Milwaukee, Wis., unless otherwise noted.
Test Methods
Test Method 1A: Dynamic Scanning Calorimetric Analysis of Homopolymer Films Each monomer was mixed with 0.1 wt % photoinitiator I-819™ (Ciba). Approximately 10 mg of each of sample was placed in the base of an open hermetic aluminum DSC pan (TA instruments TO91209). Pans were then placed in an enclosed chamber with a glass lid and ports to allow the chamber to be purged with nitrogen for 10 minutes. After purging, the chamber was placed directly under a UV lamp (365 nm, ~5 mW/cm$^2$) for 10 minutes to fully cure each sample in their respective DSC pans. Polymerized samples were individually placed on one of the sample posts in a standard differential scanning calorimeter (DSC, TA instruments) along with an empty reference pan on the opposite post. Temperature was raised to 55° C., held for 10 minutes, and then cycled between −95° C. and 55° C. twice at 3° C./min Transitions such as the crystallinity temperature (Tc) and glass transition temperature (Tg) were identified as their respective peaks in the scanning profile of heat flow vs. temperature. Typically, crystallization and melting transitions show up as positive and negative heat flow peaks as the sample is cooled and heated, and the latent heat is given off or absorbed, respectively. Conversely a glass transition is generally represented by a shift in the profile slope upon heating as the heat capacity of the sample after the transition is altered. The glass transition temperature is recorded at the inflection point of the curve associated with this shift in heat flow profile.

Test Method 1B: Dynamic Mechanical Analysis of Polymer Samples

The glass transition temperature (Tg) of high Tg materials was analyzed using a Q800 series dynamic mechanical analyzer (DMA, TA instruments, New Castle, Del.). 25.4 mm×4 mm×0.5 mm strips were cut from each cured square sample plaque using a low speed diamond saw. Samples were then placed in the thin film tensile clamps of the DMA instrument and oscillated at a constant frequency of 1 Hz with a displacement of 0.1 microns as the temperature was ramped from 25 to 200° C. The glass transition temperature of each material was determined from the peak of the tan delta vs. temperature plot generated from these tests.

Test Method 2: Dynamic Mechanical Analysis of Homopolymer Films

Dynamic mechanical analysis (DMA) of each of the homopolymers generated for Test method 1 was accomplished using an AR2000 parallel plate rheometer (TA Instruments) to characterize the thermal-mechanical properties of each sample as a function of temperature. Samples were generated by taking 2 g of each sample monomer premixed with 0.1 wt % photoinitiator (I-819™) and transferring this solution to a clamped mold comprising of a 2 mm thick silicone spacer cavity between release liners and glass plates. The mold was placed in a vertical position so that only one edge of the mold was in contact with air and then cured for 10 minutes on each glass face side with UV irradiation (365 nm, ~5 mW/cm$^2$). Post cure, the glass plates and silicone spacers were removed to leave the homopolymer film between release liners.

For each sample, approximately 0.5 g of material was centered between 8 mm diameter parallel plates of the rheometer and compressed until the edges of the sample were uniform with the edges of the top and bottom plates. The furnace doors that surround the parallel plates and shafts of the rheometer were shut and the temperature was raised to 135° C. and held for 5 minutes. The temperature was then ramped from 135° C. to −80° C. at 3° C./min while the parallel plates were oscillated at a frequency of 1 Hz and a constant % strain of 0.4%. Storage modulus (G') as a function of temperature was recorded for the temperature sweep.

Test Method 3A: Determination of Air to Nitrogen Curing Exotherm Ratio (UV Polymerization)

Each monomer was mixed with 0.1 wt % photoinitiator I-819 (BASF, Germany). Approximately 15 mg of each of sample was placed in open hermetic aluminum DSC pans (TA instruments TO91209). Pans were then placed on one of the posts of a differential photocalorimeter (DPC 2920, TA Instruments) while an empty DSC pan was placed on the reference post. A mask was placed over the DSC posts so that radiation coming from the overhead UV lamp would only directly contact the individual DSC pans. A Quartz glass panel was then placed over the mask to enclose the chamber which was then purged with either nitrogen or oxygen at a rate of 1000 cm$^3$/min. The chamber door was closed and allowed to purge for 10 minutes. The UV lamp (14 mW/cm$^2$) was then switched on for exactly 10 minutes.

The heat flow profile of each sample photopolymerization was integrated, after first subtracting the heat generated by the UV lamp baseline, to yield the total heat released from each sample. The total heat released was then normalized by dividing by the weight of the monomer initially placed in the DSC pan. The ratio of polymerization heat released per unit gram for the each monomer sample in air vs. nitrogen was then calculated.

Test Method 3B: Determination of Air to Nitrogen Curing Exotherm Ratio (Vible Light Polymerization)

The photo DSC was a TA instrument (New Castle, Del.) with DSC module 2920. The light source was a mercury/argon lamp with an Oriel PN 59480 425 nm long pass light filter. The light intensity was 3 mW/cm$^2$, measured using an International Light light meter Model IL 1400 equipped with a Model XRL, 340A detector. The photo curable samples contained 0.5% camphorquinone, 1.0% ethyl 4-(N,N-dimethylamino)benzoate, and 1.0% diphenyl iodium hexafluorophosphate as the photoinitiator package. A 10 mg cured sample was used as a reference.

About 10 mg of the sample was weighed accurately for the testing with a Hermetic Pan (aluminum sample pan) as the sample holder. The samples were equilibrated at 37° C. for 5 minutes, and then the light aperture was opened to irradiate the sample. During irradiation the sample temperature was held at 37° C. The total irradiation time was 30 minutes. After 30 minutes, the aperture was closed and the sample maintained at 37° C. for another 5 minutes. The data was collected as heat output per unit weight (mW/g). The data was analyzed using TA Thermal Solutions Universal Analysis software.

Monomers were analyzed once under nitrogen, followed by an identical sample under air. The DSC recorded the heat generation from the curing sample during exposure, and the area under the curve was integrated to give total energy in Joules/gram. The heat generated when the sample was cured in air was divided by the heat generated when the sample was cured in nitrogen to give the curing ratio. A higher ratio represents less oxygen inhibition.

Test Method 4: Peel Adhesion Strength

Peel adhesion is the force required to remove a coated flexible sheet material from a test panel measured at a specific angle and rate of removal. In the examples of this invention, the force is expressed in Newtons per width of coated sheet (Newton/dm). For each test, a 12.7 mm width of the adhesive coated sheet material approximately 10-12 cm long was cut and the release layer peeled away from the coated adhesive. The adhesive strip was then applied to the clean face of a stainless steel test panel. A heavy rubber roller was used to apply the strip. The free end of the coated strip was doubled back so that the angle of removal was 180 degrees. The free end was attached to the horizontal arm of the adhesion tester scale. The stainless steel plate was then affixed to the platform of the instrument which is mechanized to move at a controlled rate (30.5 cm/min) away from the scale. The peel test was started soon after the adhesive was applied to the substrate without allowing for an induction time for adhesion to build. The scale reading in ounces was read during the test as an average of both the peak and minimum forces during the peel. Three peel tests were run for each sample and averaged to yield the peel adhesion value. Peel adhesion was also measured for each sample using the above procedure on test panels of either stainless steel clean glass.

Test Method 5A: Adhesive Shear Strength

Shear strength of an adhesive material is directly related to the internal strength or cohesiveness of the sample and is typically quantified by the amount of force required to pull an adhesive strip from a standard flat surface with which the sample has been affixed to. Specifically, shear strength is measured in terms of the time required to pull a defined area of adhesive coated backing material from a stainless steel test panel under the stress of a constant or static load parallel to the test panel.

Shear tests were conducted using adhesive coated PET material with approximately a 0.05 mm thick adhesive coating. Cut adhesive strips were applied to a clean stainless steel panel such that a 12.7 mm by 12.7 mm portion of each strip was in firm contact with the panel and one end portion of each strip was free. The panel with adhesive strip was held in a rack such that the panel forms a 180 degree angle with the extended free end which is then tensioned by applying a one kilogram hanging weight. The time elapsed for each tape example to separate from the test panel is recorded as the shear strength in minutes. Two shear tests were performed for each sample adhesive and the shear strength averaged.

Test Method 5B: Adhesive Shear Strength

This shear test is the same as test method 5A except the cut adhesive strips were 25.4 mm by 25.4 mm in dimension.

Test Method 6: Anti-Stat Properties of Polymer Films

Average static decay was determined using the following method. Sheets of test materials were cut into 12 cm by 15 cm samples and conditioned at relative humidity (RH) of about 50% for at least 12 hours. The materials were tested at temperatures that ranged from 22-25° C. The static charge dissipation time was measured according to MIL-STD 3010, Method 4046, formerly known as the Federal Test Method Standard 10113, Method 4046, "Antistatic Properties of Materials", using an ETS Model 406D Static Decay Test Unit (manufactured by Electro-Tech Systems, Inc., Glenside, Pa.). This apparatus induces an initial static charge (Average Induced Electrostatic Charge) on the surface of the flat test material by using high voltage (5000 volts), and a field meter allows observation of the decay time of the surface voltage from 5000 volts (or whatever the induced electrostatic charge was) to 10 percent of the initial induced charge. This is the static charge dissipation time. The lower the static charge dissipation time, the better the antistatic properties are of the test material. All reported values of the static charge dissipation times in this invention are averages (Average Static Decay Rate) over at least 3 separate determinations. Values reported as >60 seconds indicate that the sample tested has an initial static charge that cannot be removed by surface conduction and is not antistatic. When the sample tested did not accept a charge of about 3000 volts or more, it was not considered to have charged sufficiently to be antistatic.

Test Method 7: Tensile Mechanical Property Analysis

Dogbone samples were tested for tensile properties using a Sintech load frame with a gap of 63.5 mm between self-tightening grips and a test speed of 25.4 mm/min to elongate and break each sample. 4 replicates were prepared for each sample and the average was determined. Elongation was determined by the change in length upon elongation of the distance between grips divided by the original length of the grip separation distance. The peak load was recorded as the highest tensile force applied to the dogbone resulting in material failure. Finally, Young's Modulus was determined as the slope of the stress vs. strain curve taken over small (0-2%) strain values.

Test Method 8: Volume Shrinkage Determination

The density of curable compositions and cured materials was measured using an AccuPyc II 1340 Pycnometer (Micromeritics, Norcross, Ga.). Ten measurements were run for each sample and the average density was determined. The volume shrinkage of the curable compositions was calculated based on the density change after curing.

volume shrinkage (%)=100×(density of cured material−density of curable material before cure)/density of curable material before cure.

Preparatory Examples 1-22

Imidazole Michael Adducts

Preparatory Example 1

The following procedure was used for the preparation of the imidazole-Michael adduct of 2-ethylhexyl acrylate (3-imidazol-1-yl-propionic acid 2-ethylhexyl ester):

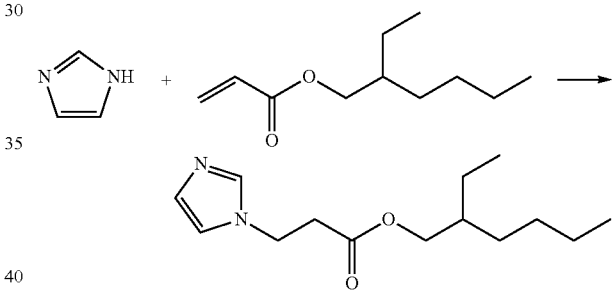

An 8 oz. (236 mL) glass jar was charged with 2-ethylhexyl acrylate (2-EHA, 92.2 g, 0.50 mol, Aldrich) and imidazole (34.0 g, 0.50 mol, Alfa Aesar). The jar was heated briefly with a heat gun until the imidazole dissolved, then the jar was placed in a 70° C. oven for 18 hours. NMR analysis of an aliquot of the reaction product indicated that no residual starting acrylate was present and that the reaction was complete. The reaction product was a light yellow colored, low viscosity oil. NMR analysis confirmed the structure of the product.

The imidazole-Michael adducts shown Table 1 were prepared by the same general procedure. In Preparatory Examples 16 and 17, the structure of the product is a representative average structure based on the molar equivalents of imidazole used.

TABLE 1

| Preparatory Example | Starting Acrylate | Imidazole-Michael Adduct |
|---|---|---|
| 2 | Isooctyl acrylate (IOA, 3M Company) |  |

TABLE 1-continued
| Preparatory Example | Starting Acrylate | Imidazole-Michael Adduct |
|---|---|---|
| 3a | Butyl acrylate | 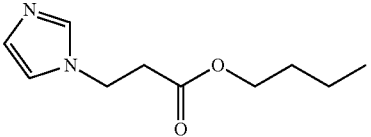 |
| 3b | Butyl acrylate | 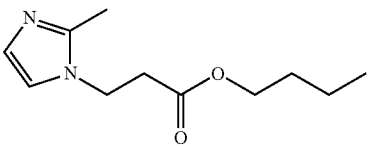 |
| 3c* | Butyl acrylate | 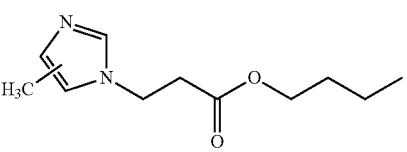 |
| 4 | Methyl acrylate | 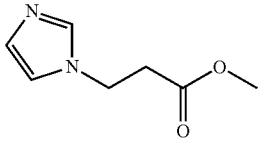 |
| 5 | Isobornyl acrylate | 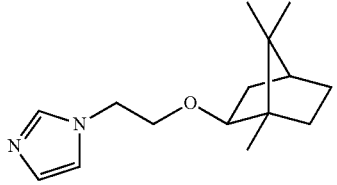 [SMILES: CC1(C)C2CCC1(C)C(OCCn1ccnc1)C2] |
| 6 | 2-Hydroxy-ethyl acrylate | 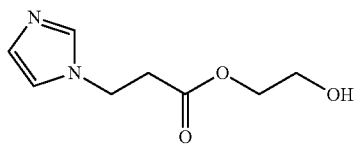 [SMILES: O=C(CCn1ccnc1)OCCO] |
| 7 | 4-Hydroxy-butyl acrylate | 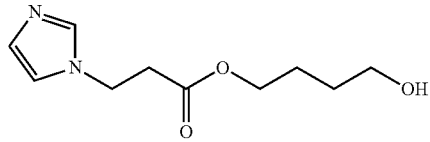 [SMILES: O=C(CCn1ccnc1)OCCCCO] |
| 8 | Tetradecyl acrylate (Hampford Research. Stratford, CT) | 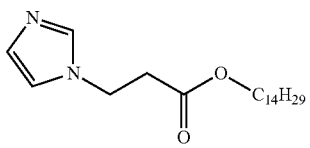 |
| 9 | 3-(Acryloyloxy)-2-hydroxypropyl methacrylate | 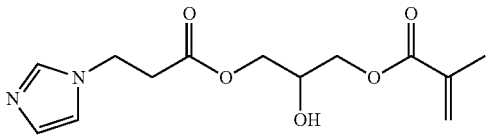 [SMILES: C=C(C)C(=O)OCC(O)COC(=O)CCn1ccnc1] |
| 10 | (2-Acryloxy) ethyl; methacrylate** | 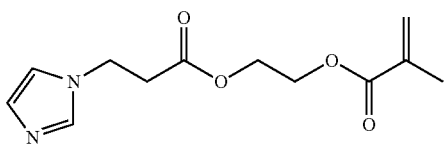 [SMILES: C=C(C)C(=O)OCCOC(=O)CCn1ccnc1] |

TABLE 1-continued

| Preparatory Example | Starting Acrylate | Imidazole-Michael Adduct |
|---|---|---|
| 11a | Tricyclo[5.2.1.0.$^{2,6}$]decanedimethanol diacrylate | |
| 11b | Tricyclo[5.2.1.0.$^{2,6}$]decanedimethanol diacrylate | |
| 11c | Tricyclo[5.2.1.0.$^{2,6}$]decanedimethanol diacrylate | |
| 12 | Polybutadiene diacrylate (Sartomer CN-307, mw~2,700) | |
| 13 | 1,6-Hexanediol diacrylate | |
| 14 | Ethoxylated bisphenol A acrylate (Sartomer SR601) | |
| 15 | Butanediol diacrylate (Sartomer SR213) | |
| 16 | Trimethylolpropane triacrylate | |

TABLE 1-continued

| Preparatory Example | Starting Acrylate | Imidazole-Michael Adduct |
|---|---|---|
| 17 | Trimethylol-propane triacrylate | *(structure: TMP with two arms as imidazole-propanoate esters and one arm as acrylate ester)* |
| 18 | Trimethylol-propane triacrylate | *(structure: TMP with all three arms as imidazole-propanoate esters)* |
| 19 | Mesityl oxide | *(structure: 4-(1H-imidazol-1-yl)-4-methylpentan-2-one)* |
| 20 | Acrylamide | *(structure: 3-(1H-imidazol-1-yl)propanamide)* |
| 21 | N,N-dimethyl-acrylamide | *(structure: 3-(1H-imidazol-1-yl)-N,N-dimethylpropanamide)* |
| 22 | Dibutyl maleate | *(structure: dibutyl 2-(1H-imidazol-1-yl)succinate)* |
| 23 | Acrylonitrile | *(structure: 3-(1H-imidazol-1-yl)propanenitrile)* |
| 24*** | Butyl methacrylate | *(structure: butyl 3-(1H-imidazol-1-yl)-2-methylpropanoate)* |

TABLE 1-continued

| Preparatory Example | Starting Acrylate | Imidazole-Michael Adduct |
|---|---|---|
| 25 | Vinyl dimethyl azlactone (3M Corporation)) | |
| 26 | Tetra (ethyleneglycol) diacrylate | |

*Product is a mixture of 3-(4-methyl-imidazol-1-yl) propionic acid butyl ester and and 3-(5-methyl-imidazol-1-yl) propionic acid butyl ester
**Prepared according to Klee, J. E., Neidhart, F., Flammersheim, H. J., and Mulhaupt, R., *Macromol. Chem. Phys.* 200, 517-523 (1999).
***Neat reaction of imidazole and butyl methacrylate at 100° C. for 5 days

Examples 1-26

Polymerizable Ionic Liquids (PILs)

The polymerizable ionic liquid monomers of the imidazole-acrylate Michael adducts were prepared by addition of a equimolar amount of a polymerizable acid functional monomer (acrylic acid (AA), methacrylic acid (MA), methacryloxydecyl phosphate (MDP, prepared according to U.S. Pat. No. 7,452,924), methacryloxyethyl phthalate (MP), methacryloxyethyl succinate (MS), acrylamidopropane sulfonic acid (AMPS), or 2-sulfoethyl methacylate (SEM, Polysciences, Inc., Warrington, Pa.)) to the appropriate imidazole-acrylate Michael adduct preparatory example.

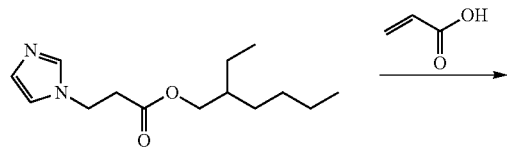

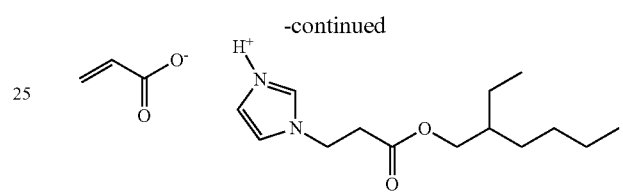

To an 8 oz. (236 mL) glass jar charged with 3-imidazol-1-yl-propionic acid 2-ethylhexyl ester (126.2 g, 0.50 mol, Preparatory Example 1) was added acrylic acid (36.0 g, 0.50 mol) and the jar was placed on a roller mill for 3 hours to mix. The product was a clear liquid.

Table 2 lists the monomers prepared and their polymer properties according to test methods 1A, 2, 3A, and 3B. C1-4 are comparative examples for monomers isooctyl acrylate (IOA), 2-ethyl hexyl acrylate (2-EHA), butyl acrylate (BA) and trimethylolpropane triacrylate (TMPTA).

TABLE 2

Properties of Acrylate and Imidazole Acrylate Monomers and Polymers

| Example | Preparatory Example | Acid Used | Polymer Tc (° C.) | Polymer Tg (° C.) | Polymer Storage Modulus @ 25° C. (MPa) | Curing Exotherm Ratio Test Method 3A | Curing Exotherm Ratio Test Method 3B |
|---|---|---|---|---|---|---|---|
| C1 | — | — | | −68 | 19,480 | 0.78 | |
| C2 | — | — | | −69 | 18,820 | 0.74 | |
| C3 | | | | −49 | 54,780 | | |
| C4 | — | — | | | | 0.98 | |
| 1 | 1 | AA | | −37 | 6,910 | 0.99 | |
| 2 | 2 | AA | | −36 | 34,770 | 0.99 | |
| 3a | 3a | AA | | −36 | 6,760 | | |
| 3b | 3b | AA | | | | | |
| 3c | 3c | AA | | | | | |
| 4 | 4 | AA | | −14 | | 0.97 | |
| 5 | 5 | AA | | 3 | | 1.04 | |
| 6 | 6 | AA | | −27 | | 0.94 | |
| 7 | 7 | AA | | −32 | | 1.00 | |
| 8 | 8 | AA | 14 | | | 0.96 | |
| 9 | 9 | AA | | | | | |
| 10 | 10 | AA | | | | | |
| 10b | 10 | MA | | | | | 0.87 |
| 10c | 10 | MDP | | | | | |

TABLE 2-continued

Properties of Acrylate and Imidazole Acrylate Monomers and Polymers

| Example | Preparatory Example | Acid Used | Polymer Tc (°C.) | Polymer Tg (°C.) | Polymer Storage Modulus @ 25° C. (MPa) | Curing Exotherm Ratio Test Method 3A | Curing Exotherm Ratio Test Method 3B |
|---|---|---|---|---|---|---|---|
| 10d | 10 | MP | | | | | |
| 10e | 10 | MS | | | | | |
| 10f | 10 | AMPS | | | | | |
| 10g | 10 | SEM | | | | | 0.92 |
| 11a | 11a | AA | | | | | |
| 11b | 11b | AA | | | | | |
| 11c | 11c | AA | | | | | |
| 12 | 12 | AA | | | | | |
| 13a | 13 | AA | | | | | |
| 13b | 13 | MA | | | | | 0.82 |
| 13c | 13 | MS | | | | | 0.89 |
| 14 | 14 | MA | | | | | 0.84 |
| 15 | 15 | MA | | | | | 0.86 |
| 16* | 16 | AA | | 30 | | 0.99 | |
| 17* | 17 | AA | | 28 | | 0.96 | |
| 18a* | 18 | AA | | 3 | | 1.04 | |
| 18b | 18 | MA | | | | | 0.96 |
| 19 | 19 | AA | | | | | |
| 20 | 20 | AA | | | | | |
| 21 | 21 | AA | | | | | |
| 22 | 22 | AA | | | | | |
| 23 | 23 | AA | | | | | |
| 24 | 24 | AA | | | | | |
| 25 | 25 | AA | | | | | |
| 26 | 26 | AA | | | | | |

*PIL monomer was mixed with 20 wt % 2-ethoxyethyl acrylate to reduce the viscosity of the monomer mixture prior to photopolymerization and analysis.

Examples 27-30

Peel Adhesive Properties of Adhesive Formulated Films

Acrylate based comparative formulations (C5-C8) were each mixed using the following procedure. 28.5 g of monomer, 0.02 g of Irgacure™ 819 (BASF), and 1.5 g of acrylic acid were mixed thoroughly in a clear glass vial. The glass vial was then purged with nitrogen for 5 minutes to remove dissolve oxygen and then placed in front of a UV light (365 nm, ~5 mW/cm$^2$) until a coatable viscosity of about 3000 cP at room temperature and acrylic conversion of approximately 10% was achieved.

Each "thickened" sample was then formulated with tackifier Foral™ 85E (Eastman Chemical Co., Kingsport, Tenn.) at 0 or 20 pph (parts per hundred relative to the resin). Additional Irgacure-651 (BASF), and photocrosslinker, XL-330 (2,4,-bis(trichloromethyl)-6-(4-methoxyphenyl)-triazine, 3M) was added at 0.09 pph and 0.08 pph respectively. As an example, 5 g of "thickened" monomer was added to an amber vial along with 1 g of Foral™ 85E tackifier (20 pph,), 0.0045 g (0.09 pph) of Irgacure™ 651, and 0.004 g (0.08 pph) of XL-330™. The amber vial was then rotated in the dark until the solid ingredients were completely dissolved. The adhesive formulation described above was coated onto primed PET film at a coating thickness of 0.05 mm and covered with a silicone treated release liner. This construction was then cured using approximately 600 mJ/cm$^2$ of UV irradiation.

PIL based formulations were generated using the following example procedure. 10 g of Preparatory Example 2, 3.5 g of acrylic acid, 0.018 g of Irgacure™ 651, 0.016 g of photocrosslinker XL-330™, and optional 2.7 g (20 pph) Foral™ 85E tackifier were well mixed. Each PIL based formulation typically had high enough viscosity that the separate "thickening" step described above was not required. The formulation was mixed in an amber jar until completely dissolved and then coated onto primed PET film at a coating thickness of 0.05 mm and covered with a silicone treated release liner. This adhesive was then cured using approximately 600 mJ/cm$^2$ of UV irradiation.

Adhesion performance of the films was tested by carrying out peel and shear tests on multiple substrates following the procedures outlined in Test Methods 4 and 5A. The failure (F) of each PSA sample is classified as adhesive failure (af), cohesive failure (cs), or partial cohesive failure (pcs).

TABLE 3

Adhesive Properties of Comparative and PIL Formulations

| Example | Monomer Example | Foral 85E Tackifier (pph) | 180 Peel on S. Steel (N/dm) | 180 Peel on Glass (N/dm) | Shear on S. Steel (min) |
|---|---|---|---|---|---|
| C5 | IOA | 0 | 29 af | 24 af | 450 |
| C6 | IOA | 20 | 116 cs | 110 cs | NT |
| C7 | 2-EHA | 0 | 28 af | 27 af | NT |
| C8 | 2-EHA | 20 | 132 cs | 136 cs | NT |
| 27 | 2 | 0 | 22 af | 7 af | 0 |
| 28 | 2 | 20 | 66 cs | 66 cs | NT |
| 29 | 1 | 0 | 24 af | 5 af | NT |
| 30 | 1 | 20 | 66 cs | 65 cs | NT |

*NT indicates that the film was not tested.

Examples 31-32

Peel Adhesive Properties of Adhesive Formulated Films

PIL based adhesive formulations were prepared using hexanediol diacrylate (HDDA) as a crosslinker. A mixture of 6.00 g of the material from Preparatory Example 1, 2.12 g of acrylic acid, 0.016 g of Irgacure™ 651, and HDDA (Table 4) were well mixed in an amber jar until completely dissolved and then coated onto primed PET film at a coating thickness of 0.08 mm and covered with a silicone treated release liner. This adhesive was then cured using approximately 600 mJ/cm$^2$ of UV irradiation. Adhesion performance of the films was tested by carrying out peel and shear tests following the procedures outlined in Test Methods 4 and 5A.

TABLE 4

Adhesive Properties of PIL Formulations

| Example | HDDA (g) | 180° Peel on S. Steel (N/dm) | Shear on S. Steel (min) |
|---|---|---|---|
| 31 | 0.008 | 9 af | 132 pcs |
| 32 | 0.016 | 11 af | 1610 af |

Examples 33-40

Addition of Bis-Imidazole to Preformed Ioa/Aa Adhesive Material

Adhesives were prepared by first generating a plastic enclosed pouch of elastomer polymer. 216 g of isooctyl acrylate (IOA), 24 g of acrylic acid, 0.036 g of isooctylthioglycolate (IOTG), and 0.168 g of Irgacure™ 651 were mixed well in an amber bottle and then 26 g of this formulation was poured and heat-sealed in a clear polyvinyl acetate pouch such as to eliminate any air bubbles. The pouch was immersed in a constant temperature water bath at 17° C. and irradiated with ultraviolet light (365 nm, 4 mw/cm^2) for eight minutes on each side to polymerize the mixture.

A 26 g adhesive pouch was added to a Brabender™ (Hackensack, N.J.) high temperature compounder and allowed to mix for 5 min at 150° C. and 100 rpm. Once the polymer appeared uniformly melted, the preparatory example imidazole compound was slowly added and allowed to mix at 150° C. and 100 rpm for 10 minutes. The mixing chamber was then cooled to 100° C. and the rotation of the mixing paddles was reversed to expel and collect polymer material.

Once cooled, approximately 1 g of the compounded material was placed between a primed PET liner (Mitsubishi) and a silicone treated release liner (Silica Nature). This construction was placed between the plates of a Carver (Wabash, Ind.) heated press with plate temperatures of 80° C. The construction was then compressed until the adhesive layer was approximately 0.05 mm in thickness. Shear adhesive tests of prepared adhesive films were performed following the procedures outlined in Test Method 5B.

TABLE 5

Adhesive Properties of Comparative and PIL Formulations

| Example | Elastomer Polymer (g) | Preparatory Example | Preparatory Example (g) | Shear on S. Steel (min) |
|---|---|---|---|---|
| C9 | 26 | None | 0 | 2,500 |
| 33 | 26 | 13 | 0.13 | 2,830 |
| 34 | 26 | 13 | 0.26 | 3,260 |
| 35 | 26 | 11a | 0.13 | 3,600 |
| 36 | 26 | 11a | 0.26 | 5,000 |
| 37 | 26 | 11b | 0.26 | 2,500 |
| 38 | 26 | 11c | 0.26 | 2,900 |
| 39 | 26 | 12 | 0.83 | 2,990 |
| 40 | 26 | 12 | 1.66 | 4,620 |

Examples 41-44

Anti-Static Properties of PIL Films

PIL films were made by first preparing a plastic enclosed pouch of polymer. As indicated in Table 6, isooctyl acrylate (IOA), acrylic acid (AA), preparatory example imidazole compound, 0.004 g isooctyl thioglycolate (IOTG), and 0.02 g of Irgacure™ 651 were mixed in an amber bottle and then 26 g of this formulation was poured and heat-sealed in a clear polyvinyl acetate pouch such as to eliminate any air bubbles. The pouch was immersed in a constant temperature water bath at 17° C. and irradiated with ultraviolet light (365 nm, 4 mw/cm$^2$) for eight minutes on each side to polymerize the formulation. Pouches of polymer were made while varying the amount of the PIL monomer as described in Table 6 below. In comparative example 10, the IOA to AA ratio by weight is 98/2. In subsequent formulations with added preparatory example 2, acrylic acid was added in excess to the amount required to generate the PIL so that approximately 2% of the overall monomer formulation comprised of acrylic acid that was not a salt with an imidazole group.

Approximately 1 g of polymer was removed from each pouch and was placed between a PET liner (Mitsubishi) and a silicone treated release liner (Silica Nature). This construction was placed between the plates of a Carver heated press (Wabash, Ind.) with plate temperatures of 80° C. The construction was then compressed until the adhesive layer was approximately 0.15 to 0.2 mm in thickness and approximately 15 cm in diameter. Each of the polymer films was tested for static decay according to Test Method 6 (Table 6).

TABLE 6

Adhesive Compositions for Anti-Static Film Characterization

| Example | IOA (g) | AA (g) | Preparatory example 2 (g) | Film Thickness (mm) | Appearance | Static Decay Time (sec) | Surface Resistivity (Ω/square) |
|---|---|---|---|---|---|---|---|
| C10 | 29.4 | 0.6 | 0.0 | 0.16 | Clear | >100 | >10E+14 |
| 41 | 29.4 | 1.2 | 3.6 | 0.18 | Hazy | >100 | >10E+14 |
| 42 | 20.9 | 2.5 | 6.6 | 0.16 | Hazy | 0.28 | 3.4E+13 |
| 43 | 12.8 | 4.3 | 12.9 | 0.16 | Clear | 0.02 | 1.2E+13 |
| 44 | 6.3 | 5.7 | 18.0 | 0.16 | Clear | 0.01 | 5.0E+12 |

Examples 44-46

In a mixing cup was placed the preparatory example imidazole and 1.44 grams acrylic acid in weights according to Table 7. The cup was speed mixed at 3000 rpm for 2 minutes for 3 cycles. 0.042 grams of Darocur™ 1173 (BASF) was added into the mixing cup and the cup was speed mixed at 3000 rpm for 2 minutes to give a clear solution.

Each formulation was coated onto PET film (available from Dupont under the trade designation "Melinex 618") with a #14 wire wound Meyer rod, to give an average thickness of about 30 microns, UV cured in a nitrogen environment with single pass at 30 feet per minute on a 6 inch UV curing processor (Fusion UV Systems Inc) equipped with a Fusion UV H bulb (on high power 100% UV that provides 58 mJ/cm$^2$ at the 30 feet per minute speed). The films were tested for anti-static decay time according to Test Method 6 (Table 7).

TABLE 7

Antistatic coatings

| Example | Preparatory Example | Preparatory Example (g) | Static decay time (s) |
|---|---|---|---|
| 44 | 2 | 5.047 | 0.01 |
| 45 | 9 | 5.646 | >100 |
| 46 | 13 | 3.62 | 0.02 |

Examples 47-49

High $T_g$ PIL Materials

Preparatory Example imidazoles 16-18 were each mixed with diethylene glycol diacrylate (DEGDA), acrylic acid (AA), and 0.2 wt % photoinitiator ethyl-2,4,6-trimethylbenzoylphenylphosphinate (TPOL, BASF) in that order (Table 8). After each formulation was well mixed, samples were poured into either a glass mold with dimensions 25.4 mm×25.4 mm×4 mm or a steel dog bone shaped mold with dimensions 112 mm (length)×7 mm (neck)×2 mm (depth). Each mold was covered with a transparent liner and then placed beneath a high intensity LED array with an output wavelength of 380 nm, 50 mW/cm$^2$, for 10 minutes to cure each sample.

Acrylate based comparative examples (C11-13) were prepared using ethoxylated trimethyloylpropane triacrylates each with a varying degree of ethoxylation (SR454, SR499, SR502; Sartomer) mixed with DEGDA to give approximately the same overall acrylate functional group concentration compared to examples 47-49. 0.2 wt % TPOL photoinitiator was added to each solution. Comparative examples were cured using the same procedures and molds as described above and analyzed using Test Methods 1B, 7, and 8 (Table 9).

TABLE 8

Formulations for High Tg Materials

| Example | Prep Example or monomer | Prep Example or monomer (g) | AA (g) | DEGDA (g) | TPOL (g) | Acrylate Conc. (mol/g) |
|---|---|---|---|---|---|---|
| 47 | 16 | 10 | 1.97 | 2 | 0.021 | 0.0072 |
| 48* | 17 | 10 | 3.33 | 6 | 0.029 | 0.0065 |
| 49 | 18 | 10 | 4.32 | 8 | 0.033 | 0.0060 |
| C11 | SR454 | 10 | | 1 | 0.017 | 0.0072 |
| C12 | SR499 | 10 | | 4 | 0.021 | 0.0065 |
| C13 | SR502 | 10 | | 5 | 0.023 | 0.0060 |

*Example 48 monomer solution was inhibited with 100 ppm Prostab 5415 (Ciba Specialty Chemicals)

TABLE 9

Physical Properties of High Tg Generated Materials

| Example | Tg (C) | Young's Modulus (MPa) | Elongation (%) | Peak Load (N) | Volume Shrinkage (%) |
|---|---|---|---|---|---|
| 47 | 144 | 20,400 | 2.6 | 1,180 | 9.3 |
| C11 | 116 | 8,200 | 3.2 | 470 | 11.0 |
| 48 | 103 | 15,400 | 3.5 | 930 | 8.4 |
| C12 | 80 | 6,100 | 4.7 | 350 | 10.7 |
| 49 | 82 | 16,900 | 4.2 | 980 | 8.8 |
| C13 | 58 | 3,500 | 7.5 | 233 | 10.4 |

The invention claimed is:

1. A polymerizable ionic liquid comprising a polymerizable anion and a cation of the formula:

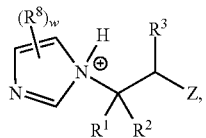

wherein
Z comprises a ketone, ester, amide, nitrile, or azlactone functional group,
$R^1$ is H or a $C_1$-$C_{25}$ alkyl group,
$R^2$ is H or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and
$R^3$ is H or $CH_3$,
$R^8$ is a (hetero)hydrocarbyl group, and w is 0, 1, 2 or 3;
with the proviso that when Z comprises a nitrile or azlactone functional group, then $R^1$ and $R^2$ is H.

2. The polymerizable ionic liquid of claim 1 comprising a cation of the formula:

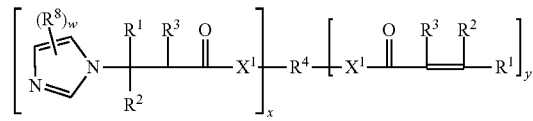

where
$R^1$ is H or a $C_1$-$C_{25}$ alkyl group,
$R^2$ is H or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and
$R^3$ is H or $CH_3$,
$R^4$ is an alkylene, cycloalkylene, or combinations thereof, optionally substituted with a hydroxyl group;
$R^8$ is a (hetero)hydrocarbyl group, and w is 0, 1, 2 or 3; and
$X^1$ is —O— or —$NR^6$—, where $R^6$ is H or a $C_1$-$C_6$ alkyl;
x is 1 to 6,
y is 0 to 5.

3. The polymerizable ionic liquid of claim 2, wherein $R^4$ is an alkylene having from 2 to 20 carbon atoms.

4. The polymerizable ionic liquid of claim 2, wherein $R^4$ is a hydroxyl-substituted alkylene.

5. The polymerizable ionic liquid of claim 1 wherein Z is

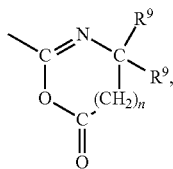

where
each $R^9$ is independently H, an alkyl group having 1 to 14 carbon atoms, and n is 0 or 1.

6. The polymerizable ionic liquid of claim 1 wherein Z is —C(O)—$X^1$—$R^{10}$, where $R^{10}$ is a hydrocarbyl group, said hydrocarbyl optionally substituted with a hydroxyl group and $X^1$ is —O— or —$NR^6$—, where $R^6$ is H or a $C_1$-$C_6$ alkyl.

7. The polymerizable ionic liquid of claim 1 wherein Z is —C(O)—$R^{10}$, where $R^{10}$ is a hydrocarbyl group, said hydrocarbyl optionally substituted with a hydroxyl group.

8. The polymerizable ionic liquid of claim 1 wherein the polymerizable anion comprises an ethylenically unsaturated polymerizable group and an acidic group selected from a carboxylic acid group (—COOH), a sulfonic acid group (—$SO_3H$), a sulfate group (—$SO_4H$), a phosphonic acid group (—$PO_3H_2$), a phosphate group (—$OPO_3H$), or a salts thereof.

9. The polymerizable ionic liquid of claim 1 wherein said anion is a (meth)acrylate.

10. The polymerizable ionic liquid of claim 1 further comprising non-acid functional, ethylenically unsaturated polar monomers.

11. The polymerizable ionic liquid of claim 1 further comprising multifunctional (meth)acrylate monomers.

12. The polymerizable ionic liquid of claim 1 comprising a polymerizable mixture of:
   i. 85 to 99.5 parts by weight of an (meth)acrylic acid ester of non-tertiary alcohol;
   ii. 0.5 to 15 parts by weight of an acid functional ethylenically unsaturated monomer;
   iii. 0 to 10 parts by weight of a non-acid functional, ethylenically unsaturated polar monomer;
   iv. 0 to 5 parts vinyl monomer; and
   v. 0 to 50 parts of a multifunctional (meth)acrylate;
   based on 100 parts by weight total monomer.

13. The polymerizable ionic liquid of claim 12 wherein the molar ratio of acid groups of the acid functional ethylenically unsaturated monomer to imidazole groups is approximately equimolar ±20%.

14. A coated article comprising a substrate, and a cured coating of the polymerizable ionic liquid of claim 1.

15. A curable composition comprising:
a) an acid-functional (meth)acrylate copolymer, and
b) a compound of the formula:

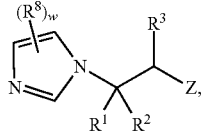

wherein
Z comprises a ketone, ester, amide, nitrile, or azlactone functional group,
$R^1$ is H or a $C_1$-$C_{25}$ alkyl group,
$R^2$ is H or —CO—$X^1$—$R^5$, where $R^5$ is a H or a $C_1$-$C_{25}$ alkyl group and $X^1$ is —O— or —$NR^6$—, where $R^6$ is H or a $C_1$-$C_6$ alkyl; and
$R^3$ is H or $CH_3$,
$R^8$ is a hydrocarbyl group, and w is 0, 1, 2 or 3;
with the proviso that when Z comprises nitrile or azlactone functional group, then $R^1$ and $R^2$ is H.

16. The curable composition of claim 15 wherein the acid-functional (meth)acrylate copolymer comprises polymerized monomer units of:
   i. 85 to 99.5 parts by weight of an (meth)acrylic acid ester monomers;
   ii. 0.5 to 15 parts by weight of an acid functional ethylenically unsaturated monomers;
   iii. 0 to 10 parts by weight of a non-acid functional, ethylenically unsaturated polar monomers;
   iv. 0 to 5 parts vinyl monomers; and
   v. 0 to 5 parts of a multifunctional (meth)acrylate monomers;
   based on 100 parts by weight total monomer.

17. The curable composition of claim 15 wherein said copolymer comprises 0.5 to 5 parts by weight of acrylic acid and 1 to 5 parts by weight of a non-acid functional, ethylenically unsaturated monomer.

18. The curable composition of claim 15 wherein the acid-functional (meth)acrylate copolymer is of the formula:

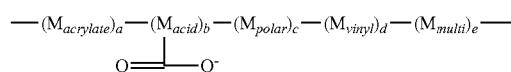

where
$M_{acrylate}$ represents polymerized multifunctional (meth)acrylate monomer units derived from (meth)acrylic acid ester of non-tertiary alcohol having "a" polymerized monomer units,
$M_{acid}$ represents polymerized monomer units derived from acid functional monomers having "b" polymerized monomer units,
$M_{polar}$ represents polymerized polar monomer units having "c" polymerized monomer units,
$M_{vinyl}$ represents polymerized vinyl monomer units derived from acid functional monomers having "d" polymerized monomer units, and
$M_{multi}$ represents polymerized multifunctional (meth)acrylate monomer units having "e" polymerized monomer units, and
wherein a and b are at least one and c, d, and e may be zero or non-zero.

* * * * *